United States Patent [19]

Hori et al.

[11] Patent Number: 4,740,058

[45] Date of Patent: Apr. 26, 1988

[54] COUPLER FOR OPTICAL INSTRUMENTS

[75] Inventors: Koichiro Hori, Framingham; Philip R. Lichtman, Newton, both of Mass.

[73] Assignee: Technology For Imaging, Inc., Framingham, Mass.

[21] Appl. No.: 902,216

[22] Filed: Aug. 29, 1986

[51] Int. Cl.[4] .......................... G02B 7/02; G02B 7/04; F16L 37/26

[52] U.S. Cl. .................................. 350/255; 285/399; 350/257

[58] Field of Search ............... 350/255, 257, 502, 508; 285/145, 309–310, 362, 367, 399; 403/338, 375, DIG. 4; 354/79

[56] References Cited

U.S. PATENT DOCUMENTS 4,135,778  1/1979  Lincoln ............................... 350/257
4,264,167  4/1981  Plummer .............................. 354/79
4,305,386  12/1981  Tawara ............................... 350/257

OTHER PUBLICATIONS

Rhodes, M. D., "Joint for Rapid Structural Assembly", NASA Tech. Briefs, 7/8-1986, pp. 117-118.

Primary Examiner—William H. Punter
Attorney, Agent, or Firm—Schiller, Pandiscio & Kusmer

[57] ABSTRACT

An opto-mechanical coupler is described for providing a quick-release mechanical and optical connection between a camera and the eyepiece of an endoscope or other optical instrument. The coupler comprises a hollow body member that is adapted to be screwed into the threaded aperture of a camera and is characterized by a center bore for transmitting images from the endoscope to the camera, and eyepiece clamping means attached to the hollow body member.

In one embodiment, the eyepiece clamping means comprises a single clamping member defining a channel for receiving the eyepiece, and means rotatably connecting the clamping means to the hollow body so that rotation of the clamping member in one direction will cause the eyepiece to be clamped to the hollow body and rotation in a second opposite direction will unclamp the eyepiece from the hollow body.

In a second embodiment, the eyepiece clamping means comprises a stationary clamping member attached to the hollow body, a movable clamping member, and means rotatably connecting the movable clamping member to the stationary clamping member so that rotation of the movable clamping member in one direction will cause the eyepiece to be clamped between the movable and stationary clamping members, and rotation of the movable clamping member in a second opposite direction will unclamp the eyepiece from the two clamping members.

The coupler includes a relay lens assembly for transmitting an image to the camera from the eyepiece. The relay lens assembly may be movable to provide variable focusing, or it may be fixed.

17 Claims, 4 Drawing Sheets

COUPLER FOR OPTICAL INSTRUMENTS

This invention pertains to opto-mechanical couplers and more particularly to the provision of a new and improved device for coupling an optical instrument eyecup or eyepiece to another optical device, e.g., a miniature TV camera.

BACKGROUND OF THE INVENTION

Although the invention has a variety of applications, it is described hereinafter in relation to microscopic surgery.

Video systems for microscopic surgery, e.g., endoscopic surgery, generally comprise a miniature TV camera, a camera control unit coupled to the camera and adapted to produce a composite video output signal, and a video monitor for displaying the image viewed by the camera. Alternatively, the composite video output signal is applied to a magnetic video tape recorder ("VCR") that in turn applies a video signal to a video monitor.

In systems for use in surgery, the camera is attached by an opto-mechanical coupler to an endoscope. As used herein, the term "endoscope" designates any form of viewing device used in micro-viewing or micro-surgery, including but not limited to arthroscopes, colonoscopes, bronchoscopes, hysteroscopes, cystoscopes, sigmoidoscopes, laparoscopes and microscopes. The opto-mechanical coupler is adapted to transmit the image seen by the endoscope to the camera and typically includes relay lenses and mechanical means for attaching the coupler to the endoscope and camera.

In surgery, it is essential that instruments that enter surgical patients be sterilizable. The same thing is true of instruments or devices that are used proximate to surgical patients. Accordingly it is desirable that the miniature TV cameras used in microsurgery and the opto-mechanical couplers associated therewith be soakable in liquid disinfecting and sterilizing solutions and also be capable of gas sterilization. It also is preferred that the camera head and the opto-mechanical coupler remain attached to each other during disinfection and sterilization. It also is desirable to have an opto-mechanical coupler that is capable of being quickly and easily connected to and disconnected from the endoscope, and also has the advantages of being (1) securely locked to both the optical viewing device and the camera and (2) accurately optically aligned with the optical viewing device and the camera.

Heretofore no opto-mechanical coupler has existed that has all or most of the foregoing desirable features.

OBJECTS OF THE INVENTION

The primary object of this invention is to provide a new, superior opto-mechanical coupler for coupling miniature TV cameras of the type used in conjunction with an endoscope.

Still another object of the invention is to provide a small, light-weight opto-mechanical coupler.

A more specific object is to provide an opto-mechanical coupler that is capable of providing a rapid connection and disconnection capability relative to an endoscope.

Another object of the invention is to provide an opto-mechanical coupler that automatically ensures the endoscope and camera are properly aligned with respect to one another.

Yet another specific object is to provide an opto-mechanical coupler that is leakproof to the extent that it and the attached camera may be immersed safely in a disinfecting or sterilizing solution Other objects and many of the attendant advantages of the invention are set forth in the following detailed description which is to be considered together with the accompanying drawings which are hereinafter described.

THE DRAWINGS

PREFERRED EMBODIMENT OF THE INVENTION

Figure 2:
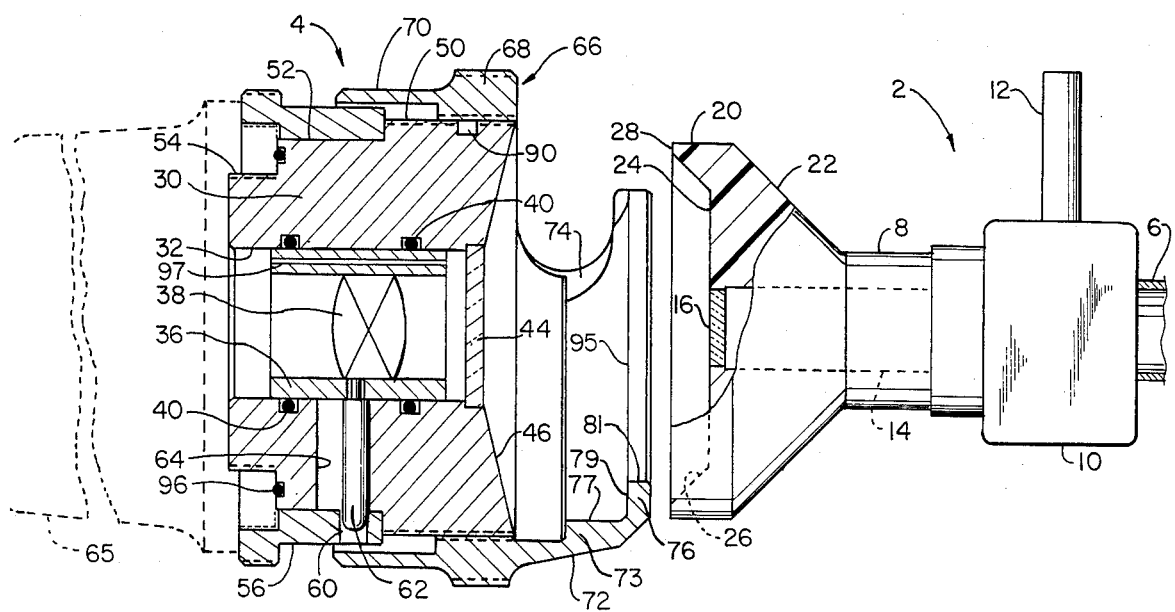
FIG. 2 is an exploded side elevation, 90° removed from the side elevation of FIG. 1, partly in section, showing the coupler of FIG. 1 and the complementary eyepiece of an endoscope.

Referring now to FIG. 2, there is shown an eypeiece 2 of an endoscope and a preferred form of opto-mechanical coupler 4 made in accordance with the the present invention.

The eyepiece 2 is of conventional construction. A hollow tube or endoscope 6 is connected to the front end or neck section of a plastic eyepiece member 8 by a hollow junction or T fitting 10. The latter has a side port 12 that is adapted to be connected by a fiber optic cable (not shown) to a light source (also not shown) for use in illuminating the field, e.g, an area of tissue or bone, that is being viewed by the endoscope. Eyepiece member 8 typically is made of a dense plastic material and has a center bore 14 fitted with eyepiece lenses (not shown) that serve to magnify and focus the real image formed by the endoscope so as to render that image perceptable by the human eye. A window 16 closes off bore 14 so as to prevent ingress of fluids It is to be noted that window 16 may constitute the rearmost lens of the eyepiece lenses in center bore 14. The rearward end of eyepiece member 8 is enlarged in the form of a peripheral flange 20 having a tapered or frusto-conical front surface 22, a flat recessed annular rear end surface 24 preferably bounded at its outer margin by a frusto-conical rear end surface 26, and a flat annular end surface 28 surrounding surface 26 at its rear end.

The coupler 4 may be made of a plastic or metal material, e.g., stainless steel or aluminum, and comprises a solid hollow body 30 having a center bore 32. The front end of bore 32 is closed off by a glass or plastic window 44 that is secured in place by suitable means. Slidably mounted within center bore 32 is a lens holder 36 that supports a relay lens assembly 38 for transmitting and focusing the image from the endoscope. The lens holder is surrounded by a multiplicity of O-rings 40 or other suitable seals (not shown) that are mounted in grooves in body 30 and serve to provide an hermetic seal between the body and lens holder while permitting the lens holder to slide in bore 32. Lens holder 36 has a small diameter hole 97 so as to permit air to flow between the front and rear ends of bore 32.

The forward end of the body 30 is provided, with a tapered or frusto-conical surface 46. The outer surface of the body 30 is characterized by a first relatively large diameter cylindrical surface 50, a second smaller diameter cylindrical surface 52, and a third still smaller diameter cylindrical surface 54 which forms an externally threaded extension. A cylindrical focusing ring 56 rotatably surrounds the rear end of hollow body 30. Ring 56 has a helical slot 60. Ring 56 is coupled to lens holder 36 by a cam follower pin 62 that has its inner end secured in a tapped radial hole in lens holder 36. Pin 62 extends through a hole 64 in hollow body 30 into slot 60. Hole 64 is elongated in a direction parallel to the axis of center bore 32 so as to permit pin 62 to move in the same direction and not in any other direction (e.g. transversely of the axis of center bore 32). The outer end of pin 62 rides in slot 60 and is engaged by one or the other of the helical surfaces of ring 56 that define the opposite sides of slot 60. Accordingly when ring 56 is rotated clockwise, pin 62 will be cammed so as to cause lens holder 36 to move lens assembly 38 in a first direction along center bore 32. Counterclockwise rotation of ring 56 will cam pin 62 so as to cause lens holder 36 to move the lens assembly in the opposite direction along center bore 32. Movement of the lens assembly is required to achieve optimum focusing of the image transmitted by the endoscope and the relay lens on the focal plane of the tv camera.

Surfaces 50 and 54 are provided with helical screw threads. The screw thread on the reduced diameter surface 54 is provided to permit the rear end of hollow body 30 to be screwed into the threaded front aperture of a miniature video camera head shown in phantom at 65. An O-ring 96 in a groove in the rear end of hollow body 30 coacts with the camera 65 to prevent any liquid from entering into the space between the camera lens and the coupler.

Still referring to FIG. 2, the purpose of the screw thread on surface 50 is to rotatably mount a cylindrical clamp member or second hollow body 66 on hollow body 30. Clamp member 66 comprises a body section in the form of a cylindrical ring section 68 that is threaded so as to provide a screw connection with the helical thread on the exterior surface 50 of hollow body 30, and an integral flange section 70 that overlaps and is spaced radially from focusing ring 56.

Figure 1:
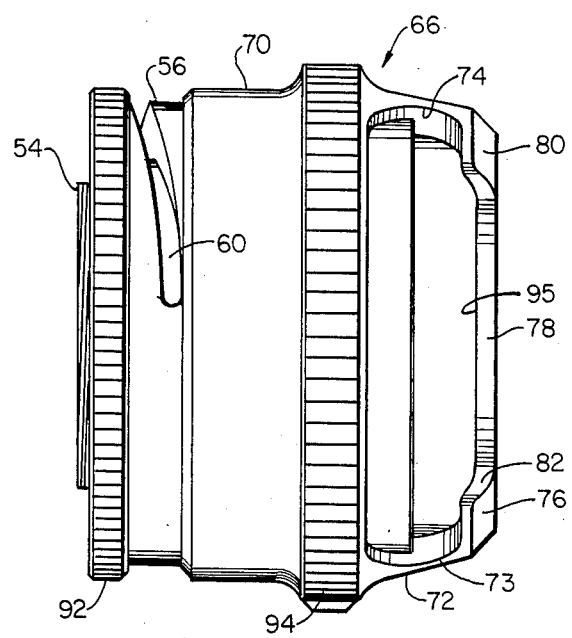
FIG. 1 is a side elevation of a preferred form of a coupler mechanism made in accordance with the present invention, with its clamp ring in extended or non-clamping position.
Figure 3:
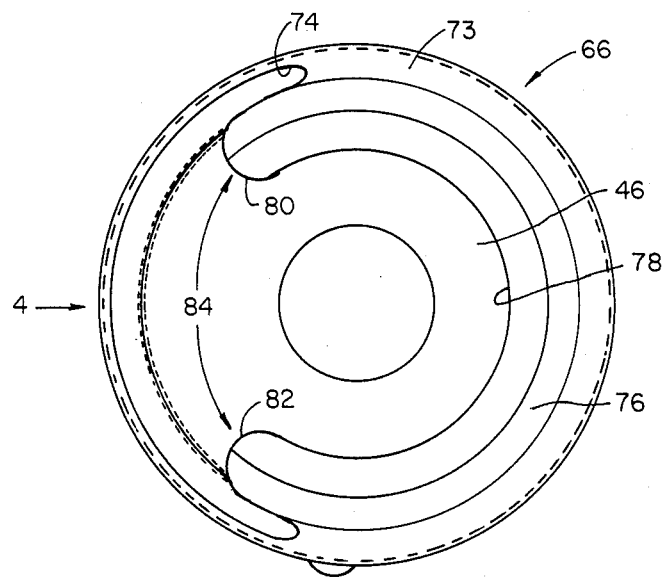
FIG. 3 is a front end elevation of the coupler mechanism of FIGS. 1 and 2.

The forward end of clamp member 66 is provided with an integrally formed clamp section 72 comprising a cylindrically shaped wall 73 that is cut away so as to form a side opening or port 74 for side entry of the endoscope eyepiece flange 20. Clamp section 72 terminates in an integrally formed C-shaped collar 76 that defines a front opening 78 (FIGS. 1–3). Side C-shaped collar 76 is split by a radially-and circumferentially-extending side opening or slot 74 opening 74 extends through an angle of approximately 150 degrees. The C-shaped collar has end portions 80 and 82 that are spaced from one another by a gap 84 (FIG. 3) of about 110 degrees that communicates with side opening 74. Wall 73 and collar 76 cooperate to define a channel for receiving the eyepiece inserted through side opening 74 and gap 84.

Figure 4:
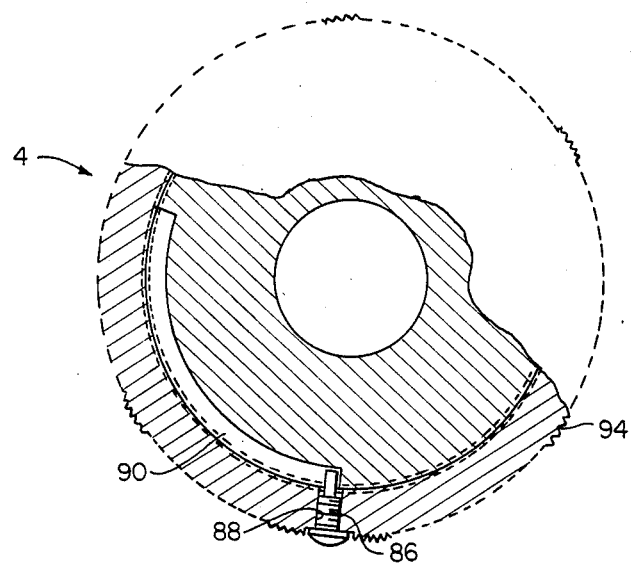
FIG. 4 is a fragmentary cross-sectional view of the the coupler mechanism of FIGS. 1 and 2, showing the mechanism for limiting rotation of the clamp ring.

Rotation of clamp member 66 on hollow body 30 is limited by a pin 86 (FIG. 4) that is screwed into a radially extending tapped hole 88 in the clamp ring and has its reduced diameter inner end disposed in a helical groove or channel 90 formed in the outer surface of hollow body 30. The width of 102 groove 90 is made large enough to allow pin 86 to move easily along the groove as the clamp member is rotated. Groove 90 extends circumferentially through an angle of preferably about 102 degrees and its helix angle is the same as that of the mating helical screw threads on the inner surface of clamp member 66 and the outer surface 50 of hollow body 30. In this connection it is to be noted that the mating screw threads on hollow body 30 and clamp member 66 have a relatively large helix angle so as to allow the clamp member to undergo an axial excursion at a relatively rapid rate, preferably at the rate of about 0.150 inch for 102 degrees of clamp member rotation. Of course, the ends of groove 90 coact with pin 86 to limit rotation of the clamp member to 102 degrees.

Preferably ring 56 and clamp member 66 have knurled surfaces 92 and 94 as shown to facilitate attachment of hollow body 30 to the camera and relative rotation of the clamp member.

Figure 5:
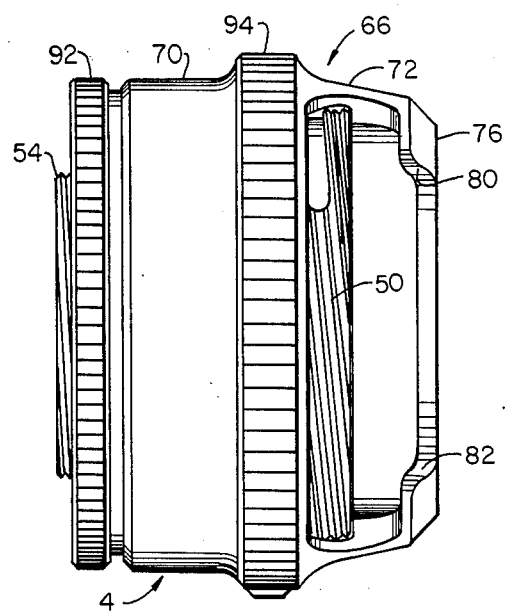
FIG. 5 is a view similar to FIG. 1 showing the clamp ring in retracted or clamping position.

In operation, the clamp member 66 is rotated so as to increase the gap between collar 76 and frusto-conical surface 46 to the maximum extent permitted by engagement of stop pin 86 with one end of groove 90 (FIG. 1). Then the rearward end of eyepiece 2 is slipped into the clamp member 66 via it side opening 74 and gap 84, so that end surface 28 of the eyepiece confronts the tapered surface 46 of hollow body 30. The members described above are sized so that if the clamp member is positioned so as to afford the maximum gap between collar 76 and hollow body 30 (FIG. 1), when the eyepiece 2 is inserted into the clamp member and held so that its end surface 28 engages the inner surface 46 of body 30, a gap of preferably about 0.100 to 0.125 inch (and necessarily less than 0.150 inch) exists between the inner edge 95 of collar 76 and the tapered surface 22 of the eyepiece. Thereafter, the clamp member is rotated so as to draw collar 76 toward tapered surface 22, thereby clamping the end surface 28 of the eyepiece against tapered surface 46 of the hollow body 30 (hollow body 30 is positioned as shown in FIG. 5 when this clamping is achieved). In this illustrated example of the invention, the inner edge 95 of collar 76 has a sharp angle and provides about 240 degrees of circular line contact with surface 22 of the eyepiece.

Alternatively, when the eyepiece is inserted into the coupler via side opening 74, it may be pulled forward so as to place front surface 22 in contact with edge 95 of collar 76, and then the clamp member may be rotated so as to draw end surface 28 into firm contact with tapered surface 46.

Because the surface 46 is tapered and inner edge 95 of collar 76 makes contact with tapered surface 22 along a major portion of the latter's circumference (e.g., about 240 degrees), automatic centering of the eyepiece with the hollow body 30 is accomplished as the clamp member is rotated to clamp the two parts together, with the result that the center bore 14 of the endoscope tube 6 is centered along the optical axis of relay lens assembly 38. With the eyepiece clamped to the coupler, focusing ring 56 may now be rotated to focus the image transmitted by the relay lens assembly 38 onto the focal plane of the camera.

Figures 6, 7:
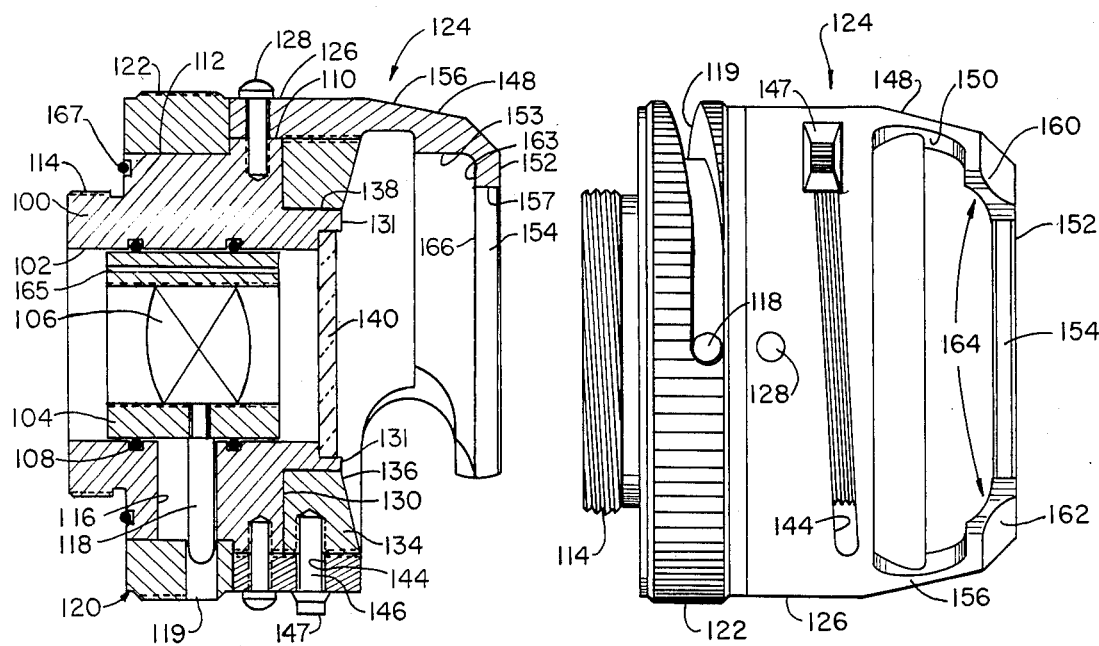
FIG. 6 is a longitudinal sectional view of an alternative form of coupler mechanism made in accordance with the present invention.
FIG. 7 is a side elevation of the coupler of FIG. 6 showing the clamp ring in extended or non-clamping position.

Referring now to FIGS. 6 and 7, there is shown an alternative embodiment of the invention that utilizes a stationary clamp member and a movable body-mounted clamp member. In this alternative embodiment the coupler mechanism comprises a hollow coupler body 100 having a center bore 102 in which is disposed a lens holder 104. A relay lens assembly 106 is mounted in lens holder 104. As with the embodiment of FIGS. 1–3, two or more O-rings 108 are mounted in the hollow body 100 so as to provide an hermetic seal between that body and the lens holder 104 while permitting the latter to be moved axially in center bore 102. Lens holder 104 has an air escape or bleeder hole 165 that provides air flow between the front and rear ends of bore 102.

The hollow coupler body 100 has a first relatively large diameter cylindrical outer surface 110 at its front end, a smaller cylindrical outer surface 112, and a still smaller cylindrical outer surface 114 at its rear end. The latter surface is provided with a screw thread so as to enable it to be screwed into the threaded aperture of a video camera (not shown).

Hollow body 100 is provided with a radially extending hole 116 that is elongated in a direction parallel to the axis of hollow body 100. Hole 116 is provided for slidably accommodating a radially-extending cam follower pin 118 that has one end anchored in the lens holder 104 and the other end projecting into a helical slot 119 formed in a focusing ring 120 that surrounds the cylindrical surface 112 of the hollow body. Focusing ring 120 is rotatable relative to hollow body 100. Preferably focusing ring 120 has a knurled surface as shown at 122. Rotation of focus ring 120 causes the lens holder 104 to move axially in the bore 102.

Mounted on the hollow body 100 is a stationary clamp member 124. The latter has a rear cylindrical ring section 126 that surrounds the forward end of hollow body 100 and is secured thereto by a plurality of threaded pins 128 that extend through holes in ring section 126 and are screwed into tapped holes in hollow body 100.

Clamp member 124 is formed with a clamp section 148 that has a side opening 150 and terminates in a C-shaped collar 152 defining a front opening 154. The construction of the shape of clamp section 148 and its collar 152 is essentially the same as that of clamp section 72 and collar 76 illustrated in FIGS. 1 and 2.

More particularly, clamp section 148 comprises a cylindrically shaped wall 156 that is cut away so as to form the side opening or port 150. At its forward end, clamp section 148 terminates in the integrally formed C-shaped collar 152 that defines the front opening 154 and has a pair of collar ends 160 and 162 that are separated by a radially and circumferentially extending gap 164. Side opening 150 extends through an angle of approximately 150 degrees. The gap 164 separating the end portions 160 and 162 subtends an angle of about 110 degrees and communicates with side opening 150. Wall 156 and collar 152 cooperate to define a channel for receiving the eyepiece inserted through side opening 150 and gap 164.

The hollow body 100 has a flat annular front end surface 130 and a small diameter extension 131 having a cylindrical outer surface 138. Rotatably mounted on extension 131 within the rear ring section 126 of stationary clamp member 124 is a movable clamp member 134 having a flat rear surface that is engageable with the flat front surface 130 of hollow body 100, and a frusto-conical forward surface 136. Center bore 102 is counterbored so as to accept a protective window 140. The latter is secured in place by suitable means, e.g., a cement. The outer cylindrical surface of clamp member 134 is threaded and mates with another screw thread formed on the inner surface of ring section 126 of stationary clamp member 124. The pitch of the screw threads on movable clamp member 134 and clamp ring 126 are selected so that rotation of clamp member 134 will cause it to move axially relative to stationary clamp member 124 at the rate of about 0.150 inch for 102 degrees of rotation.

Ring section 126 of clamp member 124 is provided with a helical slot 144 that has the same helix angle as the threads coupling movable clamp member 134 and stationary clamp member 124. Projecting into the slot 144 is a cam follower pin 146 that is screwed into a tapped hole in movable clamp member 134. Pin 146 has an enlarged head 147 located outside of clamp member 124 which functions as a knob for effecting rotation of clamp member 134.

Operation of the embodiment of FIGS. 6 and 7 to clamp it to the eyepiece 2 is similar to that of the embodiment of FIGS. 1–5. First the knob 147 is manipulated so as to cause the rotatable clamp member 134 to be drawn against the flat surface 130 of hollow body 100, thereby maximizing the gap between the frusto-conical surface 136 and the inner surface 163 of collar 152. Then the eyepiece is slipped through side opening 150 and gap 164, following which knob 147 is manipulated so as to cause clamp member 134 to be moved axially away from the flat surface 130 into engagement with end surface 28 (FIG. 2) of eyepiece 2, thereby clamping the eyepiece between the movable and stationary clamp members. As the eyepiece is brought into tight engagement with both the right angle inner edge 166 of stationary clamp member 124 and surface 136 of movable clamp member 124, the tapered surface 136 of the movable clamp member causes eyepiece 2 to be centered automatically along the optical axis of lens assembly 106. Once the eyepiece is clamped in place, the focusing ring 120 may be rotated as required to cause the lens assembly 106 to focus the image transmitted by the eyepiece optics and the relay lenses 106 onto the focal plane of the video camera (not shown).

It is to be noted that in both embodiments, the collars are characterized by a smooth cylindrical inner surface and a flat annular inner surface (surfaces 77 and 79 in the case of collar 76 in FIGS. 1–5 and surfaces 153 and 163 in the case of collar 152 in FIGS. 6 and 7) that are disposed at a right angle to one another, and the front openings of the collars are defined by flat cylindrical surfaces 81 and 157 that intersect annular surfaces 79 and 163 respectively at a right angle. As a consequence each of the collars makes a circular substantially line contact with the tapered surface 22 of the eyepiece; the circular line contact preferably extends circumferentially over a 240° arc. This line contact facilitates the automatic centering action referred to above.

Figure 8:
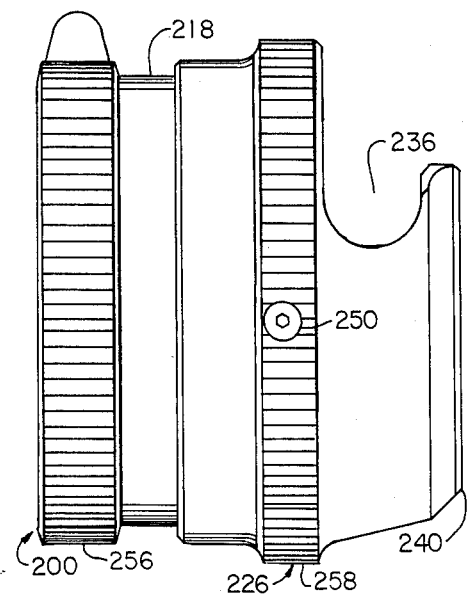
FIG. 8 is a side elevation of another possible embodiment of the invention having a fixed focus relay lens assembly.
Figure 9:
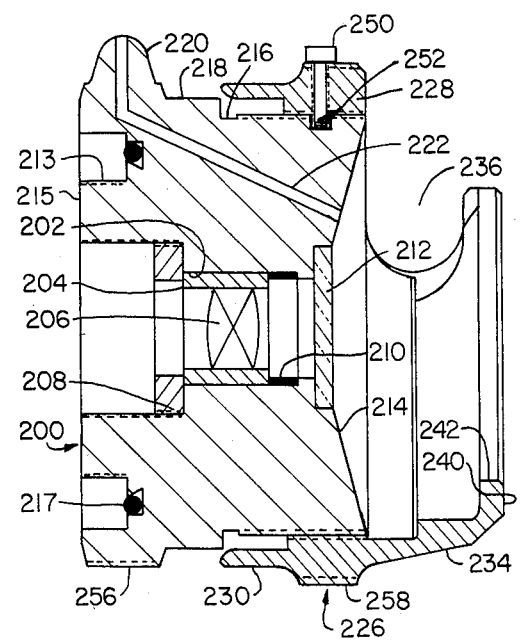
FIG. 9 is a longitudinal sectional view of the device of FIG. 8.

FIGS. 8 and 9 disclose a further embodiment of the invention in which no adjustable focusing mechanism is provided for the relay lens assembly.

The embodiment shown in FIGS. 8 and 9 comprises a solid hollow body 200 having a center bore 202 in which is mounted a lens holder 204 that supports a lens 206. Lens holder 204 is secured in a predetermined position in bore 202 by a lens retainer ring 208 screwed into a threaded counterbore at the rear end of bore 202, and a shim 210 that engages a shoulder formed by a reduction of diameter at the forward end of bore 202. Shim 210 is provided to compensate for differences in focal length of lens 206 arising from ordinary machining tolerance variations. A clear glass or plastic window 212 is secured in a counterbore in the front end of center bore 204.

Still referring to FIGS. 8 and 9, the forward end of the body 200 is provided with a tapered or frusto-conical surface 214, and the outer surface of body 200 is characterized by a first relatively small diameter cylindrical surface 216, and a second larger diameter cylindrical surface 218 having a radial extension or protuberance 220 that functions as a connecting port for a passageway 222 that extends through hollow body 200 to its tapered surface 214. Port 220 is adapted to be connected to a source of vacuum (not shown) for applying a suction force where passageway 222 intersects tapered surface 214.

The rear end of hollow body 200 has a circular groove 213 so as to define a cylindrical sleeve 215. The latter is threaded so that it may be screwed into a threaded camera lens opening. An O-ring 217 in a groove in the base of groove 213 provides an hermetic seal between the camera and body 200.

The outer surface 216 of hollow body 200 is provided with a helical screw thread that functions to rotatably mount a cylindrical clamp member 226. Clamp member 226 comprises a body section in the form of a cylindrical ring 228 that is threaded so as to provide a screw connection with the helical thread formed on the exterior surface 216, and an integral flange section 230 that is spaced radially from and is sized to overlap the surface 216 of hollow body 200.

The forward end of clamp member 226 is provided with an integrally formed clamp section comprising a cylindrically shaped wall 234 that is cut away so as to form a side opening or port 236, and an integrally formed C-shaped collar 240. Although not shown in detail, it is to be understood that the clamp section of clamp member 226 is identical to the clamp section 72 (FIGS. 1-3) of clamp member 66, with the result that a front view of clamp member 226 will reveal that it has a front opening identical to the front opening 78 of clamp section 72, and its side opening 236 extends through an angle of approximately 150 degrees. The C-shaped collar 240 has end portions (not shown) that are identical to end portions 80 and 82 and hence are spaced from one another by a gap (corresponding to gap 84 shown in FIGS. 1-3) that subtends an angle of about 110 degrees and communicates with side opening 236. Wall 234 and collar 240 cooperate to define a channel for receiving an eyepiece (similar to the one shown in FIG. 2) inserted through side opening 236 and the gap between the end portions of the collar corresponding to gap 84.

Rotation of clamp member 226 on hollow body 200 is limited by a pin 250 that is screwed into a radially extending tapped hole in the clamp member and has a reduced diameter inner end that is slidably disposed in a helical groove 252 formed in the outer surface of hollow body 200. The width of groove 252 is made large enough to allow pin 250 to move easily along the groove as the clamp member is rotated. Groove 252 extends through an angle of preferably about 102 degrees, and its helix angle is the same as that of the mating screw threads on the inner surface of clamp member 226 and the outer surface 216 of the hollow body 200. As with the previously described embodiments of the invention, the device of FIGS. 8 and 9 is characterized by the fact that the mating screw threads on hollow body 200 and clamp member 226 have a relatively large helix angle so as to allow the clamp member to undergo an axial excursion at a relatively rapid rate, preferably at the rate of about 0.150 inch for about 102 degrees of clamp member rotation. Of course, the ends of groove 252 coact with pin 250 to limit rotation of the clamp member to 102 degrees.

Preferably the outer surfaces 256 and 258 of hollow body 200 and clamp member 226 respectively are knurled to facilitate attachment of the hollow body to a camera (e.g., in the manner described above in connection with the embodiments of FIGS. 1-3) and rotation of the clamp member relative to the hollow body 200.

When the coupler device of FIGS. 8 and 9 is to be connected to an eyepiece, the clamp member is first rotated so as to increase the gap between collar 240 and Frusto-conical surface 214 to the maximum extent permitted by engagement of stop pin 250 with one end of groove 252. Then the eyepiece 2 is slipped into the clamp member via its side opening 236, so that rear end surface 28 of the eyepiece engages the tapered surface 214 of hollow body 200. The members described above are sized so that if the clamp member is positioned so as to afford the maximum gap between collar 240 and tapered surface 214 of hollow body 200, when the eyepiece 2 is inserted into the clamp member and held so that its end surface 28 engages the tapered surface 214, a gap of preferably about 0.100 to 0.125 inch (and necessarily less than 0.150 inch) exists between collar 214 and the tapered surface 22 of the eyepiece. Thereafter, the clamp member is rotated so as to draw collar 240 toward tapered surface 214, thereby clamping the eyepiece between tapered surface 214 of the hollow body and the collar 240 of the clamp member. Automatic centering of the eyepiece with the hollow body 200 is accomplished as the clamp member is rotated to clamp the two parts together, with the result that the endoscope tube 6 is centered along the optical axis of lens 206.

The preferred embodiment of FIGS. 1-5 and the alternative embodiments of FIGS. 6∝9 all offer the advantages of a quick connect and release capability, the disassociation of eyepiece 2 from the coupler being quickly achieved through the simple expedient of rotating the clamp members relative to the hollow bodies of the couplers. At the same time the couplers of FIGS. 1-7 offer a focusing capability which is desirable, and sometimes essential, to facilitate viewing and recording of the image displayed by the endoscope. The breather holes 97 and 165 are provided to permit transfer of air between the enclosed spaces on either side of lens holder 36 and the enclosed spaces on either side of lens holder 104, so as to permit free axial movement of the lens holder. The coupler is self-locking due to friction, e.g., between its clamp members and the eyepiece and also between the stationary and movable clamp members. At the same time relatively little effort is required to unlock the coupler from an eyepiece. A further advantage is that only one hand is needed to lock or unlock the coupler, a desirable feature in the case of a surgical operation where the surgeon may have only one hand free for that purpose.

A further advantage of the invention is that the couplers described above offer the capability of being sterilizable by immersion in a sterilizing liquid. In this connection, it is to be noted that when the couplers are attached to a miniature T.V. camera, the windows in the center holes of the coupler hollow bodies, e.g. the window 44 in hollow body 30, prevent liquid from invading the camera via the coupler. Of course the protective windows may be omitted if there is not need to protect against passage of fluid into the center bores.

Another important advantage is that the invention is not limited to surgical applications. Thus, opto-mechanical couplers made in accordance with this invention may be used to couple other devices and for other applications, e.g., to couple telescopes, periscopes, borescopes and night vision optical devices to still or motion picture cameras, including video cameras. By way of example, an opto-mechanical coupler made according to this invention may be used in a machinery inspecting system to couple a borescope to a still or motion picture camera.

The invention demonstrates that automatic centering of the eyepiece with the relay lens may be achieved by one or more of the following:

(a) by sizing the clamp sections 77, 153 and 259 so that they have an internal diameter that nearly matches but is slightly larger than the outside diameter of flange 20;

(b) by providing a tapered surface such as 46, 136 and 214 on the front face of the members that engage the rear end surface 28 of the eyepiece; and (c) by having a collar adapted to make a line contact with a tapered surface on the eyepiece, e.g., tapered surface 22. The ideal approach is to combine approaches (b) and (c) which makes approach (a) unnecessary and instead offers the advantage that the coupler may accommodate different diameter eyepieces.

Still other advantages will be obvious to persons skilled in the art.

What is claimed is:

1. An opto-mechanical coupler for providing a quick-release mechanical and optical connection between a video camera and the eyepiece of an endoscope, where the eyepiece defines a viewing aperture for the endoscope and comprises a hollow member having a neck section, a peripheral flange section at one end of the neck section, and an annular end surface on said flange section;

said coupler comprising a first hollow member having a center bore for providing visual communication with a video camera, and a second hollow member rotatably mounted to said first hollow member and adapted to secure said eyepiece to said first hollow member;

said first hollow member having at one end an annular end surface surrounding and concentric with said center bore and at its other end means for securing said first hollow member to the front end of a video camera;

said second hollow member comprising a ring section surrounding said first hollow member and an eyepiece clamping section, said eyepiece clamping section comprising a cylindrically curved wall encompassing a space for receiving said eyepiece and an annular collar, with one end of said wall being integral with said ring section and the other end of said wall being integral with said collar, said collar defining a front opening that communicates with the space encompassed by said wall and being split by a radially- and circumferentially-extending slot so as to form first and second mutually spaced collar end portions, said cylindrically curved wall having a side opening that communicates with said slot and extends circumferentially through an angle which is in excess of the angle subtended by said first and second collar end portions; and said first and second hollow members having mating screw threads whereby said second hollow member is capable of being moved axially along said first hollow member by relative rotation between said first and second hollow members, whereby the flange section and neck section of said eyepiece may be inserted into said space and said collar via said side opening and said slot respectively, and rotation of said second hollow member relative to said first hollow member will cause said collar to clamp the annular end surface of said flange section of said eyepiece against said annular end surface of said first hollow member.

2. A coupler according to claim 1 wherein said side opening extends circumferentially through an angle of approximately 150 degrees.

3. A coupler according to claim 1 wherein said annular end surface of said first hollow member has a conical taper.

4. A coupler according to claim 1 for use with said eyepiece wherein said peripheral flange section of said eyepiece has a conically tapered front surface concentric with its said neck section, and further wherein said collar is shaped so as to make a circular line contact with said conically tapered front surface when said second hollow member is rotated in a direction so as to cause said collar to clamp said flange section against the annular end surface of said first hollow member.

5. A coupler according to claim 1 further including a focusing lens assembly slidably disposed in said center bore, a focusing ring rotatably surrounding said first hollow member, and drive means coupling said lens assembly and said focusing ring for causing said lens assembly to move axially in said bore in a first direction or a second opposite direction as said focusing ring is rotated clockwise or counterclockwise relative to said first hollow member.

6. A coupler according to claim 5 wherein said drive means comprises a pin having one end anchored to said lens assembly, and an opposite end projecting through a radially extending hole in said first hollow member into a helical groove in said focusing ring, whereby rotation of said focusing ring will cause said pin to be cammed by an edge surface defining said helical groove along a path extending parallel to said center bore.

7. A coupler according to claim 5 further including a window disposed in the end of said center bore.

8. A coupler according to claim 1 further including a lens assembly disposed in said center bore for transmitting a real image to a focal plane located beyond said center bore.

9. A coupler according to claim 1 wherein said first hollow member has an externally threaded extension at said other end thereof.

10. An opto-mechanical coupler for providing a quick release mechanical and optical connection between a video camera and the eyepiece of an endoscope, where the eyepiece includes a hollow member comprising a neck section and a peripheral flange section at one end of said neck section, with said flange section having an annular end surface;

said coupler comprising:

a first hollow member having means for attaching said hollow member to a video camera and a center bore for providing optical communication with the aperture of said camera, a collar, a cylindrical sleeve having a first portion fixedly attached to said first hollow member and a second portion fixedly attached to and supporting said collar, said collar defining an end opening and being split by a radially and circumferentially-extending slot so as to form circumferentially spaced collar ends, said second portion of said cylindrical sleeve defining a channel and having a side opening to said channel that communicates with said slot, said side opening extending circumferentially through an angle that is in excess of the angle subtended by said slot;

an annular clamp member surrounded by said sleeve, screw threads rotatably connecting said clamp member to said sleeve whereby relative rotation of said clamp member will cause it to move axially toward and away from said collar; and means for rotating said clamp member relative to said sleeve, whereby with an eyepiece inserted into said channel via said side opening, rotation of said annular clamp member in one direction will cause said annular clamp member to engage said eyepiece and clamp its said peripheral flange portion against said collar, and rotation in the opposite direction will cause said annular clamp member to move away from said collar so as to free said eyepiece for removal from said channel.

11. A coupler according to claim 10 wherein said collar has means for providing a circular line contact with the flange section of said eyepiece when said flange section is disposed in said channel and said clamp member is rotated so as to urge said flange portion against said collar.

12. A coupler according to claim 11 wherein said flange section has a tapered front surface, and said collar engages said tapered front surface when said eyepiece is disposed in said channel and said clamp member is moved toward said collar.

13. A coupler according to claim 10 further including a focusing lens assembly slidably disposed in said center bore, a focusing ring rotatably surrounding said hollow member, and drive means coupling said lens assembly and said focusing ring for causing said lens assembly to move axially in said center bore in a first direction or a second opposite direction as said focusing ring is rotated clockwise or counterclockwise relative to said hollow member.

14. A coupler according to claim 13 wherein said drive means comprises a pin having one end anchored to said lens assembly and its opposite end projecting into a helical groove in said focusing ring.

15. A coupler according to claim 14 wherein said pin projects through an elongated hole in said hollow member.

16. A coupler according to claim 10 wherein said annular clamp member has a center hole aligned with said bore, and further including a protective window mounted in said center hole.

17. A coupler according to claim 10 wherein said side opening extends circumferentially through an angle of approximately 150 degrees.

* * * * *